US006720303B2

(12) United States Patent
Mookherjee et al.

(10) Patent No.: US 6,720,303 B2
(45) Date of Patent: Apr. 13, 2004

(54) MACROCYCLIC MUSK COMPOSITION, ORGANOLEPTIC USES THEREOF AND PROCESS FOR PREPARING SAME

(75) Inventors: Braja Dulal Mookherjee, Holmdel, NJ (US); Anubhav P. S. Narula, Hazlet, NJ (US); Michael G. Monteleone, Matawan, NJ (US); Robert W. Trenkle, Point Pleasant, NJ (US)

(73) Assignee: International Flavors & Fragrances Inc., Armonk, NY (US)

( * ) Notice: Subject to any disclaimer, the term of this patent is extended or adjusted under 35 U.S.C. 154(b) by 342 days.

(21) Appl. No.: 10/015,975

(22) Filed: Nov. 1, 2001

(65) Prior Publication Data

US 2003/0087797 A1 May 8, 2003

(51) Int. Cl.[7] .................................................. A61K 7/46

(52) U.S. Cl. ............................... 512/27; 512/8; 512/26; 568/375

(58) Field of Search ................................ 512/8, 26, 27; 568/375

(56) References Cited

U.S. PATENT DOCUMENTS 4,183,965 A 1/1980 Mookherjee et al.
6,207,274 B1 3/2001 Ferenc et al.
6,213,409 B1 4/2001 Warren et al.

OTHER PUBLICATIONS

Stork and Macdonald, Journal of the American Chemical Society, vol. 97, No. 5, Mar. 5, 1975, pp. 1264–1265.

*Primary Examiner*—Jill Warden
*Assistant Examiner*—Monique T. Cole
(74) *Attorney, Agent, or Firm*—Joseph F. Leightner

(57) ABSTRACT

Described are mixtures consisting essentially of oxomacrocyclic compounds containing greater than about 40 weight % $\Delta^3$-cyclotetradecen-1-one and greater than about 40 weight % cyclotetradecanone and less than about 5 weight %, of $\Delta^2$-cyclo-tetradecen-1-one, perfumery uses thereof and chemo-selective catalytic hydrogen process for preparing same by hydrogenating mixtures containing significant concentrations, greater than 15 weight %, of $\Delta^2$-cyclotetradecen-1-one. The oxocarbocyclic compound-containing mixtures have advantageous musk aroma imparting, augmenting and enhancing perfumery properties causing the mixtures to be useful in perfume compositions, perfumed articles and perfumed polymers, including particles and fibers produced therefrom.

15 Claims, No Drawings

MACROCYCLIC MUSK COMPOSITION, ORGANOLEPTIC USES THEREOF AND PROCESS FOR PREPARING SAME

FIELD OF THE INVENTION

The present invention relates to musk aroma-imparting, augmenting and enhancing mixtures of oxomacrocyclic compounds containing greater than about 40 weight % $\Delta^3$-cyclotetradecen-1-one and greater than about 40 weight % cyclo-tetradecanone and less than about 5 weight % $\Delta^2$-cyclotetradecen-1-one and a process for preparing such mixtures by means of a chemo-selective catalytic hydrogen of mixtures containing greater than 15% by weight of the $\Delta^2$-cyclotetradecen-1-one and greater than 45% by weight of the $\Delta^3$-cyclotetradecen-1-one.

There has been considerable work performed relating to substances which can be used to impart, alter, modify or enhance fragrances to or in various consumable materials. These substances are used to diminish the use of natural materials particularly in the musk aroma area where the use of natural materials is being replaced by the use of synthetic materials which provide more uniform and predictable properties in the finished product. Strong, substantive, sweet, warm, natural "animal-musk" aromas with an absence of oily and waxy nuances in the topnotes, middle notes and undertones, heretofore have been highly sought after by those skilled in the perfumery arts.

BACKGROUND OF THE INVENTION

Thus, prior art "animal-musk" aroma-imparting, augmenting and enhancing mixtures containing significant concentrations of cyclotetradecanone, $\Delta^2$-cyclo-tetradecen-1-one and $\Delta^3$-cyclotetradecen-1-one, for example, those disclosed in U.S. Pat. No. 4,183,965 issued on Jan. 15, 1980, the disclosure of which is incorporated herein by reference, and those disclosed by Stork and Macdonald at pages 1264 and 1265 of the Journal of the American Chemical Society, Volume 97, No.5, Mar. 5, 1975 which have desirable musk aromas all have the undesirable oily and waxy nuances present in their topnotes, middle notes and undertones, and impart these nuances to finished products produced therefrom.

Thus, nothing in the prior art discloses or suggests cyclotetradecanone/mono-unsaturated cyclotetradecen-1-one mixtures which have desirable natural "animal-musk" aromas but which have no oily and waxy nuances present in the topnotes, middle notes or undertones thereof. We have now discovered that the direct cause of the presence of such waxy and oily notes is the presence in the aroma-imparting, augmenting and enhancing mixture of significant concentrations, greater than 15 weight % on a solvent-free basis, of the isomer, $\Delta^2$-cyclotetradecen-1-one; but if the concentration, on a solvent-free basis, were to be reduced to less than 5 weight % of the mixture, the existence of the oily and waxy nuances becomes imperceptible.

Accordingly, there exists a need for a practical method to produce cyclotetradecanone/$\Delta^3$-mono-unsaturated cyclotetradecen-1-one mixtures which have the aforementioned desirable aroma properties but which have insignificant concentrations, less than 5 weight % on a solvent-free basis, of $\Delta^2$-cyclotetradecen-1-one.

SUMMARY OF THE INVENTION

Our invention is directed to strong, substantive, sweet, warm, natural "animal-musk" aroma-imparting, augmenting and enhancing macrocyclic musk compositions which are mixtures consisting essentially of oxocarbocyclic compounds containing greater than about 40 weight % $\Delta^3$-cyclotetradecen-1-one and greater than about 40 weight % cyclotetradecanone, less than 5 weight %, of $\Delta^2$-cyclotetradecen-1-one.

More specifically, our invention is directed to macrocyclic musk compositions of matter consisting essentially of:

(a) from about 40 up to about 60 weight %, on a solvent-free basis, of cyclotetradecanone;

(b) from about 40 up to about 60 weight %, on a solvent-free basis, of $\Delta^3$-cyclotetradecen-1-one; and (c) less than 5 weight %, on a solvent-free basis, of $\Delta^2$-cyclotetradecen-1-one, the weight ratio of cyclotetradecanone: $\Delta^3$-cyclotetradecen-1-one being from about 6:4 down to about 4:6.

A preferred composition of our invention consists essentially of:

(a) about 50% by weight, on a solvent-free basis, of cyclotetradecanone;

(b) about 45% by weight, on a solvent-free basis, of $\Delta^3$-cyclotetradecen-1-one; and (c) less than 5 weight %, on a solvent-free basis, of $\Delta^2$-cyclotetradecen-1-one.

The process of our invention for producing the macrocyclic musk compositions of our invention comprises the steps of:

(a) admixing a cyclotetradecenone reactant mixture comprising greater than 45% by weight of $\Delta^3$-cyclotetradecen-1-one and greater than 15% by weight of $\Delta^2$-cyclotetradecen-1-one with a hydrogenation reaction solvent to form a solvent-reactant mixture, with the weight ratio of solvent:cyclotetradecenone reactant mixture being from 20:70 up to 70:20;

(b) treating the resulting solvent-reactant mixture with hydrogen in the presence of a chemo-selective hydrogenation catalyst in a concentration of from about 0.1% up to about 0.5% by weight of the reaction mixture, at a temperature in the range of from about 15° C. up to about 35° C. and at a pressure of from about 0 psig up to about 100 psig thus forming a hydrogenated product reaction mass, whereby a composition comprising, on a solvent-free basis, greater than about 40% by weight of cyclotetradecanone, greater than about 40% by weight of $\Delta^3$-cyclotetradecen-1-one and less than about 5% by weight of Δ2-cyclotetradecen-1-one is produced; and (c) recovering the resulting macrocyclic musk composition from the hydrogenated product reaction mass (preferably by means of vacuum distillation).

DETAILED DESCRIPTION OF THE INVENTION

Several techniques for the preparation of the cyclotetradecenone reactant mixtures may be used in the practice of our invention, for example:

(a) The process described in Example I at columns 11–14 of U.S. Pat. No. 4,183,965 issued on Jan. 15, 1980, the disclosure of which is incorporated herein by reference, or (b) A process, as more particularly described herein in detail in Example I, infra, comprising the steps of (i) treating 3-hydroxycyclotetradecan-1-one in the vapor phase with a dehydrating quantity and concentration of anhydrous aluminum oxide particles, preferably from about 4 mesh up to about 8 mesh, at a dehydrating temperature, preferably from about 360° C. up to about 400° C., and pressure, preferably from about 1 mm Hg up to about 20 mm Hg, to form a dehydration product reaction mass and then (ii) recovering the cyclotetradecenone reactant mixture from the dehydration product reaction mass, preferably by means of vacuum distillation.

Preferably, the chemo-selective hydrogenation catalyst is a supported palladium catalyst containing from about 2 weight % palladium up to about 10 weight % palladium such as palladium on carbon, palladium on calcium carbonate and palladium on barium sulfate.

The hydrogenation reaction solvent is non-reactive with any reactant or reaction product, and is preferably methanol, ethanol, 2-propanol, 1-propanol, acetone, methylethylketone, methylisobutylketone, tetrahydrofuran or mixtures thereof.

A preferred set of hydrogenation reaction conditions is specifically set forth herein in Example II, infra.

Also, a preferred set of hydrogenation reaction conditions is as follows:

(i) Chemo-selective hydrogen catalyst: 5 weight % palladium on carbon;
(ii) Solvent: 2-propanol;
(iii) Hydrogenation reaction pressure: 100 psig;
(iv) Hydrogenation reaction temperature: 35° C.
(v) Weight ratio of solvent:reactant mixture: 50:50.

In carrying out the hydrogenation reaction of our invention, treatment of the solvent-reactant mixture with hydrogen causes the percentage P of $\Delta^2$-cyclotetradecen-1-one in the composition to be reduced over the period of time, θ (minutes) during which the hydrogenation takes place, according to either of the algorithms:

$$P=A(exp)(-\theta^K/\alpha)+B \quad (1)$$

or $$\theta=\{\alpha ln\,A(P-B)^{-1}\}^{1/K} \quad (2)$$

wherein θ represents the time in minutes as measured from the commencement of the hydrogenation reaction; and α, A, B and K represent constants; and wherein:

$$P\geqq 0$$

$$\theta\geqq 0;$$

$$15\leqq A\leqq 30;$$

$$0\leqq B\leqq 5;$$

$$2.8\leqq K\leqq 4.0; \text{ and}$$

$$2\times 10^3\leqq\alpha\leqq 40\times 10^3.$$

In addition, the rate of change with respect to time of the percentage of $\Delta^2$-cyclo-tetradecen-1-one, dP/dθ, in the reactant-solvent mixture being hydrogenated is according to the algorithm:

$$dP/d\theta=-AK\theta^{K-1}\alpha^{-1}(exp)(-\theta^K\alpha^{-1}).$$

The macrocyclic musk compositions of our invention and one or more auxiliary perfume ingredients, including, for example, alcohols, aldehydes, nitrites, esters, cyclic esters, ketones other than the ingredients of the macrocyclic musk compositions of our invention, hydrocarbons and natural essential oils may be admixed so that the combined odors of the individual components produce a pleasant and desired fragrance particularly and preferably in musk and "animal-like" fragrances. Such perfume compositions usually contain (a) the main note or the "bouquet" or foundation stone of the composition; (b) modifiers which round off and accompany the main note; (c) fixatives which include odorous substances which lend a particular note to the perfume throughout all stages of evaporation and substances which retard evaporation; and (d) topnotes which are usually low boiling fresh smelling materials.

In the perfume composition, it is each of the individual components which contribute to its particular olfactory characteristics, but the over-all effect of the perfume composition will be the sum of the effects of each of the ingredients. Thus, the macrocyclic musk compositions of our invention can be used to alter the aroma characteristics of a perfume composition, for example, by utilizing or moderating the olfactory reaction contributed by at least one other ingredient in the composition.

The amount of macrocyclic musk composition of our invention which will be effective in perfume compositions depends on many factors including the other ingredients, their amounts and the effects which are desired. It has been found that perfume compositions containing as little as 0.01% of the macrocyclic musk compositions of our invention and even less (e.g., 0.005%) can be used to impart sweet, warm, natural, "animal musk" aroma nuances (without oily and waxy notes) to soaps, anionic, cationic, nonionic and zwitterionic detergents, fabric softener articles, fabric softener compositions, hair preparations, cosmetics and other products. The amount employed can range up to 10% of the fragrance components and will depend on considerations of cost, nature of the end product, the effect desired on the finished product and the particular fragrance sought.

The macrocyclic musk compositions of our invention are useful, taken alone or in perfume compositions as olfactory components in anionic, cationic, nonionic and zwitterionic detergents, soaps, fabric softener compositions, fabric softener articles for use in clothes dryers (e.g., BOUNCE®, Procter & Gamble Company of Cincinnati, Ohio, U.S.A.), space odorants and deodorants, perfumes, colognes, toilet water, bath preparations such as bath oils and bath solids; hair preparations such as lacquers, brilliantines; creams; deodorants; hand lotions; sun screens; powders such as talcs, dusting powders, face powders and the like. When used as an olfactory component in perfume compositions or perfumed articles, such as anionic, cationic, nonionic and zwitterionic detergents, and in fabric softener compositions and fabric softener articles (e.g. for use in clothing dryers) as little as 0.05% of the macrocyclic musk compositions of our invention will suffice to impart a sweet, warm, natural "animal-musk" aroma, without the undesireable oily and waxy nuances. Generally no more than 5% of the macrocyclic musk composition of our invention is required in the perfume composition or in the perfumed article.

In addition, the perfume composition or fragrance composition of our invention can contain a vehicle or carrier for the macrocyclic musk compositions of our invention. The vehicle can be a liquid such as a non-toxic alcohol (e.g., ethanol) a non-toxic glycol (e.g., propylene glycol) or the like. The carrier can also be an absorbent solid, such as a gum (e.g., gum arabic, or xanthan gum) or components for encapsulating the composition (such as gelatin) as by means of coacervation. The carrier can be a microporous polymer for use in conjunction with particulate microporous polymer delivery systems, as disclosed in U.S. Pat. No. 6,213,409 issued on Apr. 10, 2001, the disclosure of which is incorporated herein by reference, or for use in conjunction with fiber delivery systems, as disclosed in U.S. Pat. No. 6,207,274 issued on Mar. 27, 2001, the disclosure of which is incorporated herein by reference.

It will thus be apparent that the macrocyclic musk compositions of our invention can be utilized to alter the sensory properties of a wide variety of consumable materials.

The following examples are illustrative and the invention is to be restricted thereto only as indicated in the appended claims. All parts and percentages given herein are by weight unless otherwise specified.

EXAMPLE I

Preparation of Mixture of $\Delta^2$-and $\Delta^3$Cyclotetradecen-1-Ones

An one liter distillation flask, equipped with a heating mantle, containing 425 gm.2-hydroxycyclotetradecan-1-one is connected directly to a 12"×1" inside diameter quartz pyrolysis tube containing 75 gm. of aluminum oxide particles having a particle size in the range of 4–8 mesh. A vacuum distillation (rushover) unit is connected directly to the quartz pyrolysis tube at the end opposite to that of the one liter distillation flask. The pyrolysis tube is heated using a high temperature Lindberg heavy duty split laboratory furnace.

The distillation flask is slowly heated to a temperature in the range of 180–200° C. thereby causing the evolution of 2-hydroxycyclotetradecan-1-one vapors. The resulting 2-hydroxycyclotetradecan-1-one vapors are thus passed into the quartz tube which is maintained at a temperature in the range of 390–400° C. under 2 mm Hg. pressure, and over the heated aluminum oxide bed thereby effecting a dehydration reaction.

The resulting reaction product is then fractionally distilled at 2.16–2.20 mm Hg at a vapor temperature of 90–140° C. using reflux ratios of 3:1 to 4:1, yielding 27 fractions. NMR, IR and mass spectral analyses confirm the following components in bulked distillation fractions 14–19:

(i) 20.7% $\Delta^2$-cycotetradecen-1-one;

(ii) 63.2% $\Delta^3$-cyclotetradecen-1-one;

(iii) 13.4% cyclotetradecanone

The resulting product has a musk aroma with waxy and oily topnotes, middle notes and undertones having a 'musk' intensity, on a scale of 1–10 of 6.5; and a substantivity on a scale of 1–10 of 8.0.

EXAMPLE II

Preparation of Mixture of Cyclotetradecanone and $\Delta^3$-Cyclotetradecen-1-One Into a 1 liter zipper autoclave equipped with a hydrogen feed line, the following ingredients are placed:

(i) 250 grams of bulked distillation fractions 14–19 of the distillation of the reaction product of Example I;

(ii) 250 grams of 2-propanol; and (iii) 0.7 grams of a 5% palladium on carbon catalyst.

The autoclave is sealed and heated to 35° C. and pressurized with hydrogen to 100 psig. Pressurization with hydrogen is maintained at 100 psig at the temperature of 35° C. for a period of 51 minutes. The autoclave is then cooled to room temperature and opened and the contents are removed and filtered. The resulting reaction mass is then admixed with 6 gm. of Primol and fractionally distilled under reduced pressure, yielding 11 fractions distilling 115–122° C. at 1.00–1.19 mm Hg pressure. Fractions 5–10 distilling at 115–122° C. are bulked. NMR, IR and mass spectral analysis confirm that the resulting product consists of: (a) 1.63% $\Delta^2$-cyclotetradecen-1-one; (b) 45% $\Delta^3$-cyclotetradecen-1-one; and (c) 50% cyclotetradecanone. The percentage of $\Delta^2$-cyclotetradecen-1-one and corresponding time of hydrogenation reaction transpired is as follows:

| TIME (MINUTES) | PERCENTAGE |
|---|---|
| 0 | 20.71 |
| 14 | 15 |
| 18 | 9.8 |
| 23 | 2.9 |
| 51 | 1.3 |

The resulting product has a sweet, warm, natural "animal-musk" aroma (without oily or waxy topnotes, middle notes or undertones) and has a substantivity of "9.5" on a scale of 1–10, and musk intensity of 9.8 on a scale of 1–10.

EXAMPLE III

Musk Perfume Formulation

The following musk perfume formulation is prepared:

| Ingredients | Parts by Weight |
|---|---|
| Musk Ambrette | 200 |
| Musk Ketone | 200 |
| GALAXOLIDE 50 ® | 140 |
| Beta Ionone | 50 |
| Vetiveryl Acetate | 50 |
| Sandalwood Oil | 100 |
| Benzyl Benzoate | 300 |
| Macreocyclic musk composition of Example II, infra, bulked distillation fractions 5–10 | 250 |

The macrocyclic musk composition of Example II imparts to this musk perfume formulation sweet, warm, natural "animal musk" undertones and topnotes (without any oily or waxy nuances).

EXAMPLE IV

Preparation of Cosmetic Compositions

A cosmetic powder is prepared by mixing in a ball mill 100 grams of talcum powder with 0.15 grams of the macrocyclic musk composition prepared according to Example II. The resulting powder has an excellent sweet, warm, natural "animal-musk" aroma (without any oily or waxy topnotes, middle notes or undertones).

A second cosmetic powder is prepared by mixing in a ball mill 100 grams of talcum powder with 0.20 grams of the perfume composition of Example III. The resulting powder has an excellent musk aroma with sweet, warm, natural "animal-musk" topnotes and undertones (without any oily or waxy nuances).

EXAMPLE V

Preparation of Soap Cake 100 grams of soap chips are prepared according to Example V of U.S. Pat. No. 4,058,490 issued on Nov. 15, 1977, the specification for which is incorporated by reference herein. The soap chips are blended in a chip mixer with 40 grams of water and 4 grams of titanium dioxide The resulting blend is then admixed with one gram of the macrocyclic musk composition of Example II until a homogeneous blend is obtained. The resulting blend is formulated into a soap cake and dried under 150 mm Hg. absolute pressure. The perfumed soap cake manifests an excellent, substantive, intense sweet, warm, natural "animal-musk" aroma (without the presence of any oily or waxy nuances).

What is claimed is:

1. A macrocyclic musk composition of matter consisting essentially of:

(a) from about 40 up to about 60 weight % of cyclotetradecanone;

(b) from about 40 up to about 60 weight % of $\Delta^3$-cyclotetradecen-1-one;

(c) less than 5 weight % of $\Delta^2$-cyclotetradecen-1-one, the weight ratio of cyclotetradecanone:$\Delta^3$-cyclotetradecen-1-one being from about 6:4 down to about 4:6.

2. The composition of matter of claim 1 consisting essentially of:

(a) about 50% by weight of cyclotetradecanone;

(b) about 45% by weight of $\Delta^3$-cyclotetradecen-1-one; and (c) less than about 2% by weight of $\Delta^2$-cyclotetradecen-1-one.

3. A process for preparing a macrocyclic musk composition comprising the steps of:

(a) admixing a cyclotetradecenone reactant mixture comprising greater than 45% by weight of $\Delta^3$-cyclotetradecen-1-one and greater than 15% by weight of $\Delta^2$-cyclotetradecen-1-one with a hydrogenation reaction solvent to form a solvent-reactant mixture with the weight ratio of solvent:cyclotetradecenone reactant mixture being from 20:70 up to 70:20;

(b) treating the resulting solvent-reactant mixture with hydrogen in the presence of a chemo-selective hydrogenation catalyst in a concentration of from about 0.1% up to about 0.5% by weight of the reaction mixture, at a temperature in the range of from about 15° C. up to about 35° C. and at a pressure of from about 0 psig up to about 100 psig thus forming a hydrogenated product reaction mass, whereby a composition comprising, on a solvent-free basis, greater than 40% by weight of cyclotetradecanone, greater than 40% by weight of $\Delta^3$-cyclotetradecen-1-one and less than 5% by weight of $\Delta^2$-cyclotetradecen-1-one is produced; and (c) recovering the resulting macrocyclic musk composition from the hydrogenated product reaction mass.

4. The process of claim 3 wherein the step of treating the solvent-reactant mixture with hydrogen causes the percentage of $\Delta^2$-cyclotetradecen-1-one in the composition to be reduced over the period of time during which the hydrogenation reaction takes place, according to the algorithm:

$$P=A(exp)(-\theta^K/\alpha)+B$$

wherein P represents the percentage of $\Delta^2$-cyclotetradecen-1-one in the mixture being reacted with hydrogen; $\theta$ represents the time in minutes as measured from the commencement of the hydrogenation reaction; and $\alpha$, A, B, and K represent constants; and wherein:

$$P \geqq 0;$$

$$\theta \geqq 0;$$

$$15 \leqq A \leqq 30;$$

$$0 \leqq B \leqq 5;$$

$$2.8 \leqq K \leqq 4.0; \text{ and}$$

$$2\times10^3 \leqq \alpha \leqq 40\times10^3.$$

5. The process of claim 4 wherein the rate of change of the percentage of $\Delta^2$-cyclotetradecen-1-one with respect to time, $dP/d\theta$, in the reactant-solvent mixture being hydrogenated is according to the algorithm:

$$dP/d\theta=-AK\theta^{K-1}\alpha^{-1}(exp)(-\theta^K\alpha^{-1}).$$

6. The process of claim 4 wherein the algorithm is:

$$\theta=\{\alpha ln\, A(P-B)^{-1}\}^{1/K}.$$

7. The process of claim 3 wherein the cyclotetradecenone reactant mixture is prepared by (i) treating 3-hydroxycyclotetradecan-1-one in the vapor phase with a dehydrating quantity and concentration of anhydrous aluminum oxide particles at a dehydrating temperature and pressure to form a dehydration product reaction mass and then (ii) recovering the cyclotetradecenone reactant mixture from said dehydration product reaction mass.

8. The process of claim 7 wherein the dehydration reaction temperature is in the range of from about 360° C. up to about 400° C. and the dehydration reaction pressure is from about 1 mm Hg up to about 20 mm Hg and the size range of each of the aluminum oxide particles is from about 4 mesh up to about 8 mesh.

9. The process of claim 3 wherein the chemo-selective hydrogenation catalyst is a supported palladium catalyst containing from about 2 weight % palladium up to about 10 weight % palladium, selected from the group consisting of palladium on carbon, palladium on calcium carbonate and palladium on barium sulfate.

10. The process of claim 9 wherein the hydrogenation reaction solvent is selected from the group consisting of methanol, ethanol, 2-propanol, 1-propanol, acetone, methylethylketone, methylisobutylketone and tetrahydrofuran.

11. The process of claim 9 wherein the chemo-selective hydrogenation catalyst is 5 weight % palladium on carbon; the hydrogenation reaction solvent is 2-propanol; the hydrogenation reaction temperature is about 35° C.; the hydrogenation reaction pressure is about 100 psig; and the weight ratio of solvent:reactant mixture is about 50:50.

12. A process for augmenting, enhancing or imparting a musk aroma in or to a consumable material selected from the group consisting of a perfume composition, a perfumed article and a perfumed polymer comprising the step of intimately admixing an aroma augmenting, enhancing or imparting quantity and concentration of the composition of claim 1 with a consumable material base.

13. A process for augmenting, enhancing or imparting a musk aroma in or to a consumable material selected from the group consisting of a perfume composition, a perfumed article and a perfumed polymer comprising the step of intimately admixing an aroma augmenting, enhancing or imparting quantity and concentration of the composition of claim 2 with a consumable material base.

14. A perfume composition comprising a perfume base and intimately admixed therewith an aroma augmenting, enhancing or imparting quantity and concentration of the composition of claim 1.

15. A perfumed article selected from the group consisting of a soap, a detergent and a cosmetic comprising a perfumed article base and intimately admixed therewith an aroma augmenting, enhancing or imparting quantity and concentration of the composition of claim 1.

* * * * *